(12) United States Patent
Suzuki et al.

(10) Patent No.: US 8,927,011 B2
(45) Date of Patent: Jan. 6, 2015

(54) METHOD FOR PRODUCING PHARMACEUTICAL TABLET

(75) Inventors: Hiroshi Suzuki, Osaka (JP); Tomohiro Yoshinari, Osaka (JP)

(73) Assignee: Toray Industries, Inc., Tokyo (JP)

( * ) Notice: Subject to any disclaimer, the term of this patent is extended or adjusted under 35 U.S.C. 154(b) by 235 days.

(21) Appl. No.: 12/601,158

(22) PCT Filed: May 20, 2008

(86) PCT No.: PCT/JP2008/059197
§ 371 (c)(1),
(2), (4) Date: Nov. 20, 2009

(87) PCT Pub. No.: WO2008/143241
PCT Pub. Date: Nov. 27, 2008

(65) Prior Publication Data
US 2010/0151016 A1    Jun. 17, 2010

(30) Foreign Application Priority Data
May 21, 2007  (JP) ................................ 2007-134421

(51) Int. Cl.
| A61K 9/20 | (2006.01) |
| A61K 31/44 | (2006.01) |
| A61K 31/485 | (2006.01) |
| A61K 47/12 | (2006.01) |

(52) U.S. Cl.
CPC ............ *A61K 9/2013* (2013.01); *A61K 9/2077* (2013.01); *A61K 31/485* (2013.01); *A61K 47/12* (2013.01)
USPC .......................................... 424/464; 514/282

(58) Field of Classification Search
None
See application file for complete search history.

(56) References Cited

U.S. PATENT DOCUMENTS

| 2004/0110781 A1 | 6/2004 | Harmon et al. |
| 2004/0137052 A1* | 7/2004 | Uchiyama et al. ............ 424/465 |
| 2005/0020613 A1 | 1/2005 | Boehm et al. |
| 2006/0040970 A1 | 2/2006 | Izumimoto et al. |
| 2007/0299100 A1 | 12/2007 | Izumimoto et al. |
| 2008/0275074 A1* | 11/2008 | Izumimoto et al. ........... 514/282 |
| 2009/0111843 A1* | 4/2009 | Kawai et al. .................. 514/282 |

FOREIGN PATENT DOCUMENTS

| EP | 1 820 505 A1 | 8/2007 | |
| WO | WO 03/055525 A1 | 7/2003 | |
| WO | WO 2004/033457 A1 | 4/2004 | |
| WO | WO 2005/094826 A1 | 10/2005 | |
| WO | WO 2006/049248 A1 | 5/2006 | |
| WO | WO2007/055184 * | 5/2007 | .......... C07D 489/00 |
| WO | WO 2007/055184 A1 | 5/2007 | |

OTHER PUBLICATIONS

Bartek, Fumaric Acid, 2004, Bartek, http://www.bartek.ca/fumaric_acid.html, pp. 1-3.*
European Search Report dated Aug. 19, 2013 for Application No. 08752993.9.
Japanese Office Action for Japanese Application No. 2009-515240 dated Mar. 12, 2013 with English translation.
Yoshihisa, "Pharmaceutical Formulation Technology", CMC Publishing Co., Ltd., Chapter 10 Tableting Procedure: Applications Parts 1 Comparison between Wet Process and Dry Process in Producing Tablets, Jul. 25, 2002, pp. 237-240.

* cited by examiner

*Primary Examiner* — Trevor Love
(74) *Attorney, Agent, or Firm* — Birch, Stewart, Kolasch & Birch, LLP

(57) ABSTRACT

A process for advantageously producing tablets having an improved release property and an excellent stability to change with time is provided. The process is for producing tablets containing a morphinan compound represented by the Formula (I) below or pharmaceutically acceptable acid addition salt thereof and an acidic substance such as fumaric acid, maleic acid or adipic acid, and characterized in that the morphinan compound or a pharmaceutically acceptable acid addition salt thereof is granulated by wet granulation together with (an) excipient(s) prior to adding the acidic substance thereto.

Formula (I):

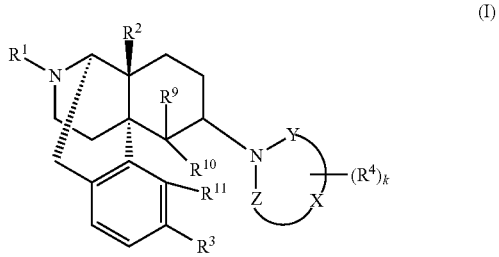

9 Claims, No Drawings

METHOD FOR PRODUCING PHARMACEUTICAL TABLET

TECHNICAL FIELD

The present invention relates to a process for producing pharmaceutically effective tablets used in the medical field, which tablets contain a morphinan compound or a pharmaceutically acceptable acid addition salt thereof.

BACKGROUND ART

In regard to compositions containing a substance which is likely to deteriorate under the neutral or alkaline condition, a technique in which an acidic substance as a pH adjuster is made to be contained in the composition to generate such a pH environment that can suppress its deterioration has been known, and in regard to compositions containing a substance which is slightly soluble under the neutral or alkaline condition, a technique in which an acidic substance as a pH adjuster is made to be contained in the composition to generate such a pH environment that can improve its solubility has been known (Patent Literature 1).
Patent Literature 1: WO 03/055525

DISCLOSURE OF THE INVENTION

Problems which the Invention Tries to Solve

In cases of compositions containing an acidic substance as a pH adjuster, a component which is slightly soluble under the neutral or alkaline condition may be chemically destabilized in the time course depending on how the acidic substance is made to be contained. Therefore, a practical, simple means for simultaneously achieving improvement in both of chemical stability and physical property of being slightly soluble under the neutral or alkaline condition is strongly demanded.

In view of the above-described circumstances, an object of the present invention is to provide a process for producing pharmaceutically effective tablets containing a morphinan compound having a nitrogen-containing heterocyclic group represented by the Formula (I) (hereinafter also referred to as "Compound (I)" for short):

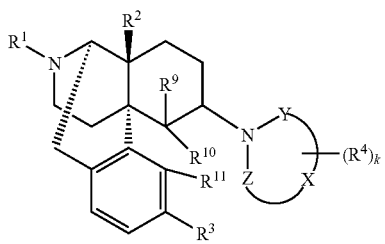

(I)

[wherein $R^1$ is hydrogen, $C_1$-$C_5$ alkyl, $C_4$-$C_7$ cycloalkylalkyl, $C_6$-$C_5$ cycloalkenylalkyl, $C_6$-$C_{12}$ aryl, $C_7$-$C_{13}$ aralkyl, $C_3$-$C_7$ alkenyl, furanylalkyl (wherein the number of carbon atoms in the alkyl moiety is 1 to 5), thienylalkyl (wherein the number of carbon atoms in the alkyl moiety is 1 to 5) or pyridylalkyl (wherein the number of carbon atoms in the alkyl moiety is 1 to 5); $R^2$ and $R^3$ independently are hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy; Y and Z independently represent valence bond or —C(=O)—; —X— represents a $C_2$-$C_7$ carbon chain (one or more of the carbon atoms therein optionally is(are) replaced by nitrogen, oxygen or sulfur atom(s), and the carbon chain optionally contains an unsaturated bond) constituting a part of the ring structure; k is an integer of 0 to 8; $R^4$ is(are) (a) substituent(s) in the number of k on the nitrogen-containing ring, which independently represent(s) fluorine, chlorine, bromine, iodine, nitro, hydroxy, $C_1$-$C_5$ alkyl, $C_7$-$C_{13}$ cycloalkylalkyl, $C_6$-$C_{12}$ aryl, $C_7$-$C_{13}$ aralkyl, $C_7$-$C_{1-3}$ aralkyloxy, $C_1$-$C_5$ alkoxy, trifluoromethyl, trifluoromethoxy, cyano, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_p NR^7R^8$ or $(CH_2)_pN(R^7)COR^8$, or among the $R^4$s in the number of k, two $R^4$s bound to the same carbon atom or to the same sulfur atom together represent one oxygen atom to form carbonyl or sulfoxide, or two $R^4$s bound to the same carbon atom together represent one sulfur atom to form thiocarbonyl, or four $R^4$s bound to the same sulfur atom together represent two oxygen atoms to form sulfone, or among the $R^4$s in the number of k, two $R^4$s bound to adjacent carbon atoms, respectively, together form benzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of said fused rings is non-substituted or substituted by 1 or more $R^5$s, wherein $R^5$(s) independently represent(s) fluorine, chlorine, bromine, iodine, nitro, hydroxy, $C_1$-$C_5$ alkyl, $C_1$-$C_5$ alkoxy, trifluoromethyl, trifluoromethoxy, cyano, $C_6$-$C_{12}$ aryl, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$; $R^9$ is hydrogen, $C_1$-$C_5$ alkyl, $C_1$-$C_5$ alkenyl, $C_7$-$C_{13}$ aralkyl, $C_1$-$C_3$ hydroxyalkyl, $(CH_2)_pOR^6$ or $(CH_2)_pCO_2R^6$; $R^{10}$ and $R^{11}$ are bound to form —O—, —S— or —$CH_2$—, or $R^{10}$ is hydrogen and $R^{11}$ is hydrogen, hydroxy, $C_1$-$C_5$ alkoxy or $C_1$-$C_5$ alkanoyloxy; p is an integer of 0 to 5; $R^6$ is hydrogen, $C_1$-$C_5$ alkyl, $C_3$-$C_7$ alkenyl, $C_6$-$C_{12}$ aryl or $C_7$-$C_{13}$ aralkyl; and $R^7$ and $R^8$ independently are hydrogen, $C_1$-$C_5$ alkyl or $C_7$-$C_{13}$ aralkyl]
or a pharmaceutically acceptable acid addition salt thereof (hereinafter Compound (I) and a pharmaceutically acceptable acid addition salt thereof are inclusively referred to as "Compound (I) species" for short).

Means for Solving the Problem

The present inventors intensively studied to find that, when tablets containing Compound (I) species and an acidic substance are produced by separately granulating Compound (I) species together with an excipient by wet granulation and then adding an acidic substance to the granulated Compound (I) species, the tablets surprisingly have an excellent shelf stability to change with time concurrently with the improved solubility of Compound (I) species, thereby completing the present invention.

That is, the present invention is as follows.

[1] A process for producing tablets containing a Compound (I) species and an acidic substance, which process is characterized in that the Compound (I) species is granulated by wet granulation together with (an) excipient(s) prior to adding the acidic substance thereto.

[2] The process according to [1] above, wherein the Compound (I) species and the acidic substance are separately granulated by wet granulation together with (an) excipient(s), respectively.

[3] The process according to [1] above, wherein the Compound (I) is N-[(5R,6R,14S)-17-(cyclopropylmethyl)-4,5-epoxy-3,14-dihydroxymorphinan-6-yl]phthalimide.

[4] The process according to [1] above, wherein the acidic substance is one or more substances selected from the group consisting of fumaric acid, maleic acid, adipic acid and salts thereof.
[5] The process according to [1] above, wherein the acidic substance is added at an amount of 0.01 to 500 parts by weight per 1 part by weight of the Compound (I) species.
[6] The process according to [1] above, wherein the content of the acidic substance is 0.001 to 85% (w/w) based on the entire tablet.
[7] The process according to [1] above, wherein the content of the acidic substance is 0.001 to 85% (w/w) based on a plain tablet.
[8] The process according to [1] above, wherein a fine powder, not less than 90% by weight of which has a particle size of not more than 355 µm, is used as the acidic substance.
[9] The process according to [1] above, wherein a fine powder, not less than 90% by weight of which has a particle size of not more than 250 µm, is used as the acidic substance.
[10] The process according to [1] above, wherein a powder of the acidic substance is added.
[11] The process according to [1] above, wherein a solution or a partially dissolved suspension of the acidic substance is added.
[12] A tablet obtained by the process according to [1] above.
[13] A tablet produced by adding an acidic substance to granules containing a Compound (I) species, which granules are made by wet granulation.

Effects of the Invention

By the present invention, a process for producing tablets which show an improved release of a Compound (I) species and have an excellent shelf stability to change with time, while suppressing the deterioration during the production, can be provided.

BEST MODE FOR CARRYING OUT THE INVENTION

The present invention will now be described in more detail.
As for Compound (I) species, it is preferred that both Y and Z be —C(=O)— or both Y and Z be valence bonds.
In cases where both Y and Z are —C(=O)—, $R^1$ is preferably hydrogen, $C_4$-$C_7$ cycloalkylalkyl, $C_6$-$C_8$ cycloalkenylalkyl, $C_6$-$C_{12}$ aryl or $C_3$-$C_7$ alkenyl, more preferably hydrogen, cyclopropylmethyl, 2-cyclopropylethyl, 3-cyclopropylpropyl, 4-cyclopropylbutyl, cyclobutylmethyl, cyclopentylmethyl, cyclohexylmethyl, 2-cyclobutenylethyl, 3-cyclobutenylpropyl, phenyl, naphthyl, tolyl, allyl or prenyl. Among these, especially preferred are hydrogen, cyclopropylmethyl, cyclobutylmethyl, cyclopentylmethyl, cyclohexylmethyl, allyl and prenyl. $R^2$ is preferably hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy. Among these, hydrogen, hydroxy, methoxy, ethoxy, allyloxy, benzyloxy, acetoxy and propionoxy are preferred, and hydrogen, hydroxy, methoxy and acetoxy are especially preferred. $R^3$ is preferably hydrogen, hydroxy, $C_1$-$C_5$ alkoxy, $C_7$-$C_{13}$ aralkyloxy or $C_1$-$C_5$ alkanoyloxy, more preferably, hydrogen, hydroxy, methoxy, ethoxy, benzyloxy, acetoxy or propionoxy. Among these, hydrogen, hydroxy, methoxy and acetoxy are especially preferred. The "—X—" is preferably $C_2$-$C_4$ carbon chain constituting a part of the ring structure, more preferably a carbon chain having two carbon atoms constituting a part of the ring structure. The "k" is preferably an integer of 0 to 6. $R^4$ is preferably $C_1$-$C_5$ alkyl, $C_7$-$C_{13}$ aralkyl, $C_7$-$C_{13}$ aralkyloxy, or two $R^4$s bound to adjacent carbon atoms, respectively, together form benzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of the fused rings is non-substituted or substituted by 1 or more $R^5$s. More preferably, $R^4$ is methyl, ethyl, ethylidene, propyl, propylidene, butyl, butylidene, benzyl, benzylidene, methylbenzyl, methylbenzylidene, fluorobenzyl, fluorobenzylidene, trifluoromethoxybenzyl, trifluoromethoxybenzylidene, phenethyl, phenethylidene, cyclohexylmethyl, cyclohexylmethylidene, phenoxy, chlorophenoxy or to form benzene fused ring. Especially preferably, two $R^4$s together form benzene fused ring which is not substituted or substituted by 1 or more, preferably 1 to 4 substituent $R^5$s. Although the benzene fused ring which is not substituted is also preferred, the substituent(s) $R^5$(s) is(are) preferably and independently fluorine, chlorine, bromine, iodine, nitro, $C_1$-$C_5$ alkyl (especially methyl, ethyl or propyl), $C_7$-$C_{13}$ aralkyl (especially benzyl), hydroxy, $C_1$-$C_5$ alkoxy (especially methoxy or ethoxy), trifluoromethyl, trifluoromethoxy, cyano, phenyl, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$ (wherein p is an integer of 0 to 5; $R^6$ is hydrogen, $C_1$-$C_5$ alkyl (especially methyl, ethyl or propyl), $C_3$-$C_7$ alkenyl or $C_6$-$C_{12}$ aryl (especially phenyl); $R^7$ and $R^8$ independently are hydrogen, $C_1$-$C_5$ alkyl (especially methyl, ethyl or propyl), or $C_7$-$C_{13}$ aralkyl (especially benzyl)). The benzene fused ring is more preferably non-substituted, or substituted by one or more $R^5$s selected from the group consisting of fluorine, chlorine, bromine, iodine, nitro, methyl, ethyl, propyl, benzyl, hydroxy, methoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, acetoxy, phenyloxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl and amino. $R^9$ is preferably hydrogen, $C_1$-$C_5$ alkyl, allyl or benzyl, more preferably hydrogen or methyl. $R^{10}$ and $R^{11}$ are preferably bound to form —O—, or $R^{10}$ is preferably hydrogen and $R^{11}$ is preferably hydrogen, hydroxy or methoxy. Especially preferably, $R^{10}$ and $R^{11}$ are bound to form —O—.

On the other hand, in cases where both Y and Z are valence bonds, $R^1$ is preferably hydrogen, $C_1$-$C_5$ alkyl, $C_7$-$C_{13}$ aralkyl, furanylalkyl (wherein the number of carbon atoms in the alkyl moiety is 1 to 5), thienylalkyl (wherein the number of carbon atoms in the alkyl moiety is 1 to 5) or pyridylalkyl (wherein the number of carbon atoms in the alkyl moiety is 1 to 5), more preferably hydrogen, methyl, ethyl, propyl, benzyl, phenethyl, phenylpropyl, 2- or 3-furanylmethyl, 2- or 3-furanylethyl, 2- or 3-furanylpropyl, 2- or 3-thiophenylmethyl, 2- or 3-thiophenylethyl, 2- or 3-thiophenylpropyl, 2-, 3- or 4-pyridinylmethyl, 2-, 3- or 4-pyridinylethyl, or 2-, 3- or 4-pyridinylpropyl. Among these, hydrogen, methyl, phenethyl, furanylethyl, thiophenylethyl and pyridinylethyl are especially preferred. $R^2$ is preferably hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy. Among these, hydrogen, hydroxy, methoxy, ethoxy, allyloxy, benzyloxy, acetoxy and propionoxy are preferred, and hydrogen, hydroxy, methoxy and acetoxy are preferred. $R^3$ is preferably hydrogen, hydroxy, $C_1$-$C_5$ alkoxy, $C_7$-$C_{13}$ aralkyloxy or $C_1$-$C_5$ alkanoyloxy, more preferably, hydrogen, hydroxy, methoxy, ethoxy, benzyloxy, acetoxy or propionoxy. Among these, hydrogen, hydroxy, methoxy and acetoxy are especially preferred. The "—X—" is preferably $C_4$-$C_6$ carbon chain constituting a part of the ring structure, or the above-mentioned carbon chain in which one or two carbon atoms is(are) replaced by oxygen, sulfur or nitrogen atom(s). Among these, especially preferred are carbon chain having 5 carbon atoms constituting a part of the ring structure and the carbon chain just mentioned above in which one carbon atom is replaced by oxygen, sulfur or nitrogen atom. The "k" is preferably an integer of 0 to 6. $R^4$ is preferably $CONR^7R^8$ (wherein $R^7$ and $R^8$ are independently hydrogen, methyl, ethyl, propyl or benzyl), or preferably two $R^4$s bound to adjacent carbon atoms, respectively, together form benzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of the fused rings is non-substituted or substituted by 1 or more, especially 1 to 4 $R^5$s. $R^4$ is more preferably dimethylamide or diethylamide, or to form the benzene fused ring. Other $R^4$(s) is(are) preferably and independently methyl, ethyl, propyl or benzyl, or two $R^4$s bound to the same carbon atom preferably represent one oxygen atom to form carbonyl. Especially preferably, the carbon atom adjacent to the above-mentioned carbonyl group is replaced by nitrogen atom to form an amide bond. Although the benzene fused ring which is not substituted is also preferred, the substituent(s) $R^5$(s) is(are) preferably and independently fluorine, chlorine, bromine, iodine, nitro, $C_1$-$C_5$ alkyl (especially methyl, ethyl or propyl), $C_7$-$C_{13}$ aralkyl (especially benzyl), hydroxy, $C_1$-$C_5$ alkoxy (especially methoxy or ethoxy), trifluoromethyl, trifluoromethoxy, cyano, phenyl, isothiocyanato, $SR^6$, $SOR^E$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$ (wherein p is an integer of 0 to 5; $R^6$ is hydrogen, $C_1$-$C_5$ alkyl (especially methyl, ethyl or propyl), $C_3$-$C_7$ alkenyl or $C_6$-$C_{12}$ aryl (especially phenyl); $R^7$ and $R^8$ independently are hydrogen, $C_1$-$C_5$ alkyl (especially methyl, ethyl or propyl), or $C_7$-$C_{13}$ aralkyl (especially benzyl)). The benzene fused ring is more preferably non-substituted, or substituted by one or more substituent $R^5$s selected from the group consisting of fluorine, chlorine, bromine, iodine, nitro, methyl, ethyl, propyl, benzyl, hydroxy, methoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, acetoxy, phenyloxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl and amino. $R^9$ is preferably hydrogen, $C_1$-$C_5$ alkyl, allyl or benzyl, more preferably hydrogen or methyl. $R^{10}$ and $R^{11}$ are preferably bound to form —O—, or $R^{10}$ is preferably hydrogen and $R^{11}$ is preferably hydrogen, hydroxy or methoxy. Especially preferably, $R^{10}$ and $R^{11}$ are bound to form —O—.

Representative examples of the Compound (I) used in the present invention include N-(17-cyclopropylmethyl-4,5α-epoxy-3,14-dihydroxy-morphinan-6β-yl)-phthalimide (i.e., N-[(5R,6R,14S)-17-(cyclopropylmethyl)-4,5-epoxy-3,14-dihydroxymorphinan-6-yl]phthalimide, hereinafter referred to as "Compound A" for short). The Compound (I) species may be produced according to, but not limited to, WO2004/033457 or Tetrahedron, 50, 9757, (1994).

As for Compound (I) species in the present invention, examples of the pharmaceutically acceptable acid addition salt include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt, methanesulfonic acid salt and the like are preferred, but the acid addition salt is not restricted thereto.

The process according to the present invention is a process for producing tablets containing a Compound (I) species and an acidic substance, which process is characterized in that the Compound (I) species is granulated by wet granulation together with (an) excipient(s) prior to adding the acidic substance thereto.

The process according to the present invention comprises the steps of (1) granulating the Compound (I) species together with (an) excipient(s) by wet granulation, and (2) adding an acidic substance to the granules obtained in step (1).

Step (1), Wet Granulation of Compound (I) Species and Excipient(s)

Examples of the wet granulation include fluid bed granulation, tumbling fluidized bed granulation, centrifugal granulation, stirring granulation, spray granulation, and extrusion granulation. In the present invention, fluid bed granulation is preferred, and the granulation may be carried out by a conventional method, for example, as follows: (i) the compound (I) species and (an) excipient(s) are mixed in a fluid bed granulator, or preliminarily mixed and placed in a fluid bed granulator, and then the mixture is granulated while spraying a binding solution under fluidization, or (ii) (an) excipient(s) is(are) placed in a fluid bed granulator and granulated while spraying a binding solution containing the Compound (I) species under fluidization.

Usually the resulting granules are dried subsequently to the granulation. As required, the granules may be subjected to size selection using an appropriate disintegrator such as a power mill.

The granules obtained in Step (1) are hereinafter also referred to as "main drug granules".

In the present specification, a process for producing tablets wherein particles composed of an acidic substance are added to the granules (or the size-selected granules) produced by wet granulation of the Compound (I) species and (an) excipient(s) is defined as "two-group granulation process".

The content of the Compound (I) species in a tablet is not restricted, and usually 0.0001 to 90% (w/w) based on the entire tablet.

The Compound (I) species used in the production of tablets of the present invention is preferably such a fine powder that not less than 90% by weight thereof has a particle size of preferably not more than 850 μm, more preferably not more than 500 μm, especially preferably not more than 150 μm. The lower limit of the particle size of the Compound (I) species is not restricted. In a conventional dry pulverization using a jet mill or the like, not less than 90% by weight of the obtained powder has a particle size of ten and several μm, and such a fine powder may appropriately be used in the present invention.

In cases where not less than 90% by weight of the Compound (I) species is not more than 850 μM, the advantage that the dissolution rate of the Compound (I) species is high can be obtained.

In the present specification, the particle size is a value measured by a laser diffraction analyzer for dry measurement (e.g., Mastersizer 2000, Malvern).

The content of the Compound (I) species in the main drug granules is not restricted, and usually 0.0001 to 90% (w/w) based on the main drug granules.

It is preferred that 90% by weight of the main drug granules have the particle size of not more than 1500 μm, more preferably not more than 1000 μm, especially preferably not more than 850 μm. The particle size of not more than 1500 μm is advantageous to the content uniformity and the weight variation of the resulting tablets. Although the lower limit of the particle size is not restricted, extremely fine particles whose size is, for example, not so different from the size before granulation, may possibly cause tableting problems.

If large particles exist in main drug granules, size selection may be carried out to obtain the desired particle size. Main drug granules comprising particles of not more than 1500 μm in an amount of less than 90% may have a drawback in the content uniformity or the weight variation.

Step (2), Addition of Acidic Substance to Main Drug Granules

In the present invention, a procedure for adding an acidic substance to main drug granules is not restricted as long as both of them are contained in a tablet.

Tablets produced by adding an acidic substance to main drug granules according to the present invention may be obtained by, for example, mixing main drug granules, an acidic substance and (an) optional additive(s) and then compressing the mixture with a tableting machine or the like. Tablets of the present invention may also be obtained as a multilayer tablet or a dry coated tablet or the like by compressing a composition which contains main drug granules and (an) optional additive(s) and a composition which contains an acidic substance and (an) optional additive(s) in steps.

The "acidic substance" used in the present invention is preferably an acidic substance which is non-hygroscopic. The term "non-hygroscopic" means that "the weight change at moisture absorption equilibrium is 5% or less at 80% relative humidity RH". Hygroscopicity may be evaluated by measuring the weight change at moisture absorption equilibrium. Briefly, a sample is kept in a desiccator or the like at the prescribed humidity until the weight of the sample which is absorbing moisture reaches equilibrium, and then the sample is dried in accordance with the method described in the Japanese pharmacopoeia, 13th Edition, followed by calculating the change in weight due to drying as the weight of the absorbed moisture. As an acidic substance, one or a combination of two or more acidic substances selected from the group consisting of fumaric acid, maleic acid, adipic acid and salts thereof is especially preferred.

In the process for producing tablets according to the present invention, the amount of the used acidic substance is preferably 0.001 to 500 parts by weight, more preferably 0.01 to 500 parts by weight, especially preferably 0.1 to 500 parts by weight per 1 part of the Compound (I) species. In cases where less than 0.001 part by weight of an acidic substance is used, improvement in the release property of the Compound (I) species may be insufficient, or its release may be delayed due to change with time. In cases where more than 500 parts by weight of an acidic substance is used, suppression of the deterioration of the Compound (I) species during the production may be insufficient, or the shelf stability to change with time may not always be extremely excellent.

The content of an acidic substance in the tablet is not restricted, and preferably 0.0001 to 95% (w/w), more preferably 0.0001 to 90% (w/w), especially preferably 0.001 to 85% (w/w) based on the entire tablet.

The content of an acidic substance in the plain tablet is not restricted, and preferably 0.0001 to 95% (w/w), more preferably 0.0001 to 90% (w/w), especially preferably 0.001 to 85% (w/w) based on the entire plain tablet.

In the present specification, a "plain tablet" refers to a tablet obtained without any special steps except screening inspection after tableting. Plain tablets may be the final product in some cases.

On the other hand, a "tablet" refers to a tablet obtained by subjecting a plain tablet to (a) special step(s) besides screening inspection, such as, for example, a film-coated tablet produced by subjecting a plain tablet to a film coating step. Besides a film coating step, examples of such a step include a press coating step and a dry-coating step.

The acidic substance used in the production of tablets of the present invention is preferably such a fine powder that not less than 90% by weight thereof has a particle size of preferably not more than 850 μm, more preferably not more than 500 μm, still more preferably not more than 355 μm, especially preferably not more than 250 μm. The lower limit of the particle size is not restricted. In a conventional dry pulverization using a jet mill or the like, not less than 90% by weight of the obtained powder has a particle size of ten and several μm, and such a fine powder may appropriately be used in the present invention.

In cases where not less than 90% by weight of the acidic substance has the particle size of not more than 850 μm, the effect of addition of the acidic substance is high, and the amount of the acidic substance to be added may advantageously be decreased.

If large particles exist in the acidic substance contains, size selection may be carried out to obtain the desired particle size.

The form of the acidic substance when mixed with the main drug granules is not restricted. For example, granules obtained by granulating the acidic substance together with (an) excipient(s) or the like, a powder of the acidic substance, and also a solution or a partially dissolved suspension of the acidic substance may be used.

Examples of the granulation method used in cases where the acidic substance is granulated together with (an) excipient(s) or the like include dry granulation, crystallization and spray granulation besides the above-described wet granulation.

Examples of the excipient used in the present invention include lactose, starch, corn starch, crystalline cellulose (e.g., Avicel PH-101 (trade name), produced by Asahi Kasei), powdered sugar, granulated sugar, mannitol, light anhydrous silicic acid and L-cysteine. These excipients may be used either individually or in combination. The content of the excipient(s) in the tablet of the present invention is preferably about 0.1 to about 99.5% by weight, more preferably about 0.1 to about 99% by weight, still more preferably about 0.1 to about 98% by weight.

In two-group granulation process, main drug granules and particles composed of the acidic substance may be made as multilayer tablets such as bilayer or trilayer tablets, or dry coated tablets or press coated tablets, without mixing up the main drug granules and the acidic substance particles.

On the other hand, in the two-group granulation process, main drug granules and particles composed of the acidic substance may be mixed to make partitioned tablets in which the granules and the particles are partitioned at a certain distance from each other (i.e., main drug granules and acidic substance particles are contained in a tablet such that the granules and the particles are not in contact with each other).

As described below, (an) optional additive(s) may be contained in the tablet according to the present invention. It should be noted that, in cases where a lubricant is used for the above-mentioned partitioned tablet, the hardness of the obtained tablets may usually be unacceptable in practice or the release from the obtained tablets may usually reach a plateau if too long a time is spent on mixing a lubricant. Therefore, usually (an) optional additive(s) except a lubricant, main drug granules and particles composed of an acidic substance are mixed at first, and then a lubricant is added to the thoroughly mixed mixture, followed by mixing for a short time to complete the mixing step. In the present specification, mixing of the components except a lubricant is defined as the first mixing, and mixing with a lubricant is defined as the second mixing. In cases where the first mixing is finished in a short time, the first and second mixing steps may be carried out at the same time.

Examples of the two-group granulation process include (1) a production process wherein main drug granules and granules (or size-selected granules) obtained by wet granulation of an acidic substance and (an) excipient(s) are mixed, and (2) a production process wherein main drug granules and acidic substance particles having an appropriate particle size are mixed.

In the first mixing step, the mixing ratio of main drug granules and particles of acidic substance is, but not limited to, preferably 1:30 to 1:0.00001 in weight, more preferably 1:20 to 1:0.00001 in weight, especially preferably 1:10 to 1:0.00001 in weight, in view of the mixing uniformity. If the mixing ratio is out of this range, it will take a long time to attain uniform mixing, and segregation may occur during the tableting step. "Mixing uniformity" (or simply "uniformity") as used herein refers to the uniformity of the Compound (I) species. The uniformity follows the content uniformity defined in codices such as the Japanese pharmacopoeia.

In view of the mixing uniformity similarly to above, the bulk density (mL/g) of main drug granules and particles composed of an acidic substance is, but not limited to, preferably 1:4 to 1:0.25, more preferably 1:3 to 1:0.3, especially preferably 1:2 to 1:0.5. In cases where the bulk density is out of this range, it will take a long time to attain uniform mixing, and segregation may occur during the tableting step. However, in cases where the amount of the particles composed of an acidic substance to be added is small, there may be no problem even if the bulk density is out of this range. In the present specification, bulk density is calculated by dividing volume (mL) of granules or size-selected granules by weight (g) thereof.

In view of the mixing uniformity similarly to above, although the size distribution of main drug granules and particles composed of acidic substance in the first mixing step is not restricted thereto, it is preferred that the percentage of particles having the same size in the granules and the particles be within ±100% by weight, more preferably within ±70% by weight, especially preferably within ±50% by weight. In cases where the particle size distribution of both particles is not equal or almost equal, it will take a long time to attain uniform mixing, and segregation may occur during the tableting step. However, in cases where the percentage of particles having the same size is relatively low and where the amount of particles composed of an acidic substance to be added is small, there may be no problem even if the percentage is out of this range.

In view of the mixing uniformity similarly to above, in the first mixing step, although the content of the main drug granules by size is not restricted thereto, it is preferred that the content of particles of each size be within the content of main drug granules±100%, more preferably within the content of main drug granules±50%, especially preferably within the content of main drug granules±20%. In cases where the content is not equal or almost equal, it will take a long time to attain uniform mixing, and segregation may occur during the tableting step. However, in cases where the weight of each size fraction is relatively low or where the amount of the particles composed of an acidic substance to be added is small, there may be no problem even if the content is out of this range.

In the present invention, (a) pharmaceutically acceptable additive(s) (e.g., binders, disintegrants, lubricants, coating agents, antiseptics, antioxidants, coloring agents, light shielding agents, flavoring agents, correctives and the like) may be contained besides the above-mentioned excipients.

Examples of the above-mentioned binder include sucrose, gelatin, powdered acacia, methylcellulose, hydroxypropylcellulose, hydroxypropylmethylcellulose, carboxymethylcellulose, sodium carboxymethylcellulose, polyvinylpyrrolidone, pullulan, and dextrin. These binders may be used individually or in combination. The content of the binder(s) in the tablet of the present invention is preferably about 0.01 to about 30% by weight, more preferably about 0.03 to about 10% by weight.

Examples of the above-mentioned disintegrant include croscarmellose sodium (e.g., Ac-Di-Sol), cross-linked insoluble polyvinylpyrrolidone (e.g., Kollidon CL produced by BASF), low substituted hydroxypropylcellulose, partially-alphanized starch, carmellose (e.g., NS-300 produced by GOTOKU CHEMICAL CO. LTD.), carmellose sodium (e.g., ECG-505 produced by GOTOKU CHEMICAL CO, LTD. or the like), enteric polymers (e.g., hydroxypropylmethylcellulose phthalate, cellulose acetate phthalate, carboxymethylcellulose or the like), and water-insoluble polymers (e.g., aminoalkyl metaacrylate copolymer, methacrylate copolymer or the like). These disintegrants may be used individually or in combination. The content of the disintegrant(s) in the tablet of the present invention is preferably about 0.1 to about 10% by weight, more preferably about 0.5 to about 7% by weight.

Examples of the above-mentioned lubricant include magnesium stearate and talc. Examples of the above-mentioned coloring agent include tar dye, caramel, red iron oxide, titanium oxide, and riboflavins.

Examples of the above-mentioned coating agent include hydroxypropylcellulose, hydroxypropylmethylcellulose, polyvinyl alcohol, polyvinylpyrrolidone-vinyl acetate copolymer, cellulose ethyl ester, wax, enteric polymers (e.g., hydroxypropylmethylcellulose phthalate, cellulose acetate phthalate, carboxymethylcellulose or the like), and water-insolubility polymer (e.g., aminoalkyl metaacrylate copolymer, methacrylate copolymer or the like). As required, plasticizers, stabilizers, and the like such as polyethylene glycol, dibutyl sebacate, diethyl phthalate, triacetin and triethyl citrate may be used. The amount of the coating material is preferably about 0.01 to about 100% by weight, more preferably about 0.1 to about 80% by weight, most preferably about 2 to about 50% by weight based on the core (plain tablet). It is preferred that coloring agents, light shielding agents and the like be further contained. Examples of the above-mentioned coloring agent and light shielding agent include tar dye, caramel, red iron oxide, yellow iron oxide, titanium oxide, and riboflavins.

A pan coating machine or the like is usually used for the film coating operation. Film-coated tablets may be those obtained by coating round tablets, oval tablets or oblong tablets with a film.

In spraying a film coating solution, the temperature of the product (tablets) is usually controlled within about 10° C. to 100° C., preferably about 30° C. to 80° C., more preferably about 35° C. to 60° C.

Moreover, formulation additives such as stabilizers, flavoring agents, sweeteners, correctives, antiseptics, antioxidants, light shielding agents and the like may be contained.

The formulation of tablets obtained by the production process of the present invention may be, for example, a plain tablet of a round or oval shape tablet, or a coated tablet thereof. The formulation may also be a partitioned tablet obtained by mixing and tableting two or more kinds of granules, a multilayer tablet such as a bilayer tablet or trilayer tablet, a dry coated tablet, a press coated tablet or the like.

The tablets may be given the sustained release property (prepared as a sustained release preparation) by giving an appropriate release control function thereto. In cases of film coated tablets, the release control function may be given to a film composition, or plain tablets per se may be given the release control function by a technique such as wax matrix tablets, water-soluble matrix tablets or the like.

The tablets according to the present invention are suitable for ensuring long-term absorption which is particularly required by sustained release preparations. That is, the tablets of the present invention are effective for attaining sustained release of slightly soluble materials, since slightly soluble materials hardly dissolve and therefore the absorption thereof is likely to decrease in the lower digestive tract where moisture is relatively low compared to the upper digestive tract.

In cases where the wettability of the Compound (I) species and the acidic substance used in the present invention is bad, formulation techniques may be employed to improve the wettability. For example, (an) agent(s) for improving wettability may be contained in the tablet, or surface modification may be employed.

An agent for improving wettability may be used without limitation as long as the agent can improve the wettability. Examples of the agent for improving wettability include non-ionic surfactants (e.g., polyoxyethylene alkyl ether, polyethylene glycol fatty acid ester, polyoxypropylene alkyl ether, polypropylene glycol fatty acid ester, sorbitan fatty acid ester, polyoxyethylene sorbitan fatty acid ester, polyoxyethylene hydrogenated castor oil, polyglycerol fatty acid ester, polyoxyethylene glycerol fatty acid ester, glycerol mono-fatty acid ester, alkyl polyglucoside, polyoxyethylene polyoxypropylene block polymer, alkanolamide and the like), amphoteric surfactants (e.g., betaine alkyldimethylaminoacetate, betaine amidepropyldimethylaminoacetate, amide amino acid salts, alkyl iminodiacetic acid salts and the like), anionic surfactants (e.g., alkyl sulfuric acid ester salts, alkyl ether sulfuric ester salts, α-olefin sulfonic acid salts, acyl methyl taurine salts, acyl glutamic acid salts, acyl glycine salts, acyl sarcosine salts, acyl isethionic acid salts, alkyl ether carboxylic acid salts, amide ether sulfuric acid ester salts, alkyl phosphoric acid ester salts and the like), cationic surfactants (e.g., alkyltrimethylammonium chloride, dialkyldimethylammonium chloride and the like), bile acid and salts thereof, soap and fatty acid and salts thereof, oil, glycerol fatty acid ester, enamine, chelating agents, phenothiazine, fatty acid derivatives of carnitine or peptide, azone, concanavalin A, (a) substance(s) selected from the group consisting of diethyl maleate and diethyl ethoxymethylene malonate, products of Maillard reaction, and polymers (e.g., block copolymer and biodegradable polymer, chitosan and derivatives thereof). Among these, preferred are surfactants (amphoteric surfactants, anionic surfactants, cationic surfactants), hydrophilic polymers, cyclodextrin derivatives, cholic acid derivatives and the like, and especially preferred are surfactants. Among surfactants, anionic surfactants are preferred, and long chain alkyl sulfuric acid salts (the number of carbon atoms is preferably 10 to 20) are more preferred, and sodium lauryl sulfate is most preferred. "Sodium lauryl sulfate" as mentioned herein is a single substance. In the present invention, agents for improving wettability may be used individually or in combination.

The agent for improving wettability may be contained in the tablets by adding thereto the agent in form of a powder, or a solution of the subject substance to be improved in wettability and (an) agent(s) for improving wettability in an appropriate solvent or a suspension in which either of them is partially dissolved may be added during the production process. In this case, the addition of the agent(s) for improving wettability may result in the surface modification. In selecting an appropriate solvent, consideration should be paid to safety and stability when the solvent remains. Although water is most preferred, organic solvents, oils, and organic liquids which has melted under heat such as wax may be used. The solvent may also be a mixed solution prepared by mixing these organic liquids in water.

In cases where a solution of the subject substance to be improved in wettability and (an) agent(s) for improving wettability in an appropriate solvent or a suspension in which either of them is partially dissolved may be added during the production process, if drying step is performed, the solution or suspension may be converted into a powder by spray drying, lyophilization, vacuum drying or the like to use as a solid composition in the form of powder. Aggregation inhibitors, antistatic agents and the like may be added in the powderization as required. Examples of the aggregation inhibitor include anticaking agents such as talc, corn starch, hydrated silicon dioxide, light anhydrous silicic acid and magnesium aluminometasilicate, saccharides such as lactose, and sugar alcohols such as mannitol and trehalose. Examples of the antistatic agent include talc, hydrated silicon dioxide and light anhydrous silicic acid.

The above-mentioned drying step may be employed in combination with a step such as fluid bed granulation, tumbling fluidized bed granulation or centrifugal granulation. A solution of the subject substance to be improved in wettability and (an) agent(s) for improving wettability in an appropriate solvent or a suspension in which either of them is partially dissolved may be directly sprayed as a binder solution to obtain granules. In this case, an additional binder may be added as required. The solution or suspension may also be simply added during stirring granulation or extrusion granulation.

In addition to the above-mentioned spray drying, lyophilization, vacuum drying or the like, the above-mentioned powderization may be carried out by a method in which, using as a solvent wax or the like which has melted under heat, a liquid composition prepared by dissolving or suspending the subject substance and the agent in the wax is allowed to solidify at room temperature, and the obtained solid is pulverized. The powderization may also be carried out by a method wherein wax or the like which has melted under heat is further added to a suspension of the powder obtained in this step, and the mixture is allowed to solidify at room temperature, followed by pulverization of the obtained solid.

The content of the agent(s) for improving wettability is not restricted, and preferably 0.00001 to 100 parts by weight, more preferably 0.00001 to 10 parts by weight, especially preferably 0.0001 to 5 parts by weight per 1 part of "the subject substance to be improved in wettability".

In cases where a solution of the subject substance to be improved in wettability and (an) agent(s) for improving wettability in an appropriate solvent or a suspension in which either of them is partially dissolved is used, the solid content in the liquid is, but not limited to, preferably 0.01 to 1000% (wt/wt), more preferably 0.1 to 500% (wt/wt), especially preferably 1 to 100% (wt/wt). The "solid content" as used herein is calculated by dividing the sum of the weight of the subject substance to be improved in wettability and (an) agent(s) for improving wettability contained in the solution or suspension by the weight of the liquid.

Besides the addition of the agent for improving wettability, examples of the surface modification as a procedure for improving wettability include a method in which the subject substance to be improved in wettability and the agent(s) for improving wettability are mixed using a tumbler mixer or the like and the mixture is used for surface coating, a method in which the subject substance and the agent(s) are subjected to dry granulation using a dry granulator such as a roller compactor, a method in which the subject substance and the agent(s) are subjected to wet granulation using a wet granulator such as fluid bed granulator, tumbling fluidized bed granulator or centrifugal granulator.

The present invention will now be described in more detail by way of a comparative example, example and experiment thereof. However, the present invention is not restricted by the examples below.

EXAMPLES

Comparative Example 1-1

Compound A (26.6 g), D-mannitol (318.1 g), and crystalline cellulose (42.6 g, CEOLUS, grade PH101, Asahi Kasei) were uniformly mixed, and the mixture was made to pass through a sieve with mesh size of 850 μm to uniformly mix again. The resulting mixed powder was placed in a fluid bed granulator/dryer (LAB-1, Powrex), and granulated while spraying an aqueous solution of 5% (wt./v) hydroxypropylcellulose (255.3 g, grade L, Nippon Soda) under fluidization, and thereafter dried to obtain granules. The obtained granules were made to pass through a sieve with mesh size of 850 μm to obtain main drug granules.

To main drug granules (380.1 g), croscarmellose sodium (20.2 g, Ac-Di-Sol) and magnesium stearate (4.0 g, Taihei Chemical Industrial) were added and mixed to obtain granules for tableting. The obtained granules were tabletted with a tableting machine using a round-shaped punch and die with a diameter of 7.5 mm to obtain 160 mg plain tablets. The obtained plain tablets were placed in a film coating machine (HICOATER, Freund Corporation), and sprayed with a liquid in which titanium oxide, macrogol 6000 (Sanyo Chemical), iron sesquioxide, and hydroxypropylmethylcellulose 2910 (TC-5, grade RW, Shin-Etsu Chemical) were dissolved or dispersed, thereby obtaining film tablets containing 10 mg of Compound A, 119.6 mg of D-mannitol, 16 mg of crystalline cellulose, 4.8 mg of hydroxypropylcellulose, 8 mg of croscarmellose sodium, 1.6 mg of magnesium stearate, 5.8 mg of hydroxypropylmethylcellulose 2910, 1.4 mg of macrogol 6000, 0.6 mg of titanium oxide, and 0.2 mg of iron sesquioxide per a tablet.

Comparative Example 1-2

Compound A (19.9 g), D-mannitol (178.7 g), crystalline cellulose (31.9 g, CEOLUS, grade PH101, Asahi Kasei), and fumaric acid (59.8 g) were uniformly mixed, and the mixture was made to pass through a sieve with mesh size of 850 μm to uniformly mix again. The resulting mixed powder was placed in a fluid bed granulator/dryer (LAB-1, Powrex), and granulated while spraying an aqueous solution of 5% (wt./v) hydroxypropylcellulose (191.5 g, grade L, Nippon Soda) under fluidization, and thereafter dried to obtain granules. The obtained granules were made to pass through a sieve with mesh size of 850 μm to obtain main drug granules.

To main drug granules (270 g), croscarmellose sodium (14.4 g, Ac-Di-Sol) and magnesium stearate (2.9 g, Taihei Chemical Industrial) were added and mixed to obtain granules for tableting. The obtained granules were tabletted with a tableting machine using a round-shaped punch and die with a diameter of 7.5 mm to obtain 160 mg plain tablets. The obtained plain tablets were placed in a film coating machine (HICOATER, Freund Corporation), and sprayed with a liquid in which titanium oxide, macrogol 6000 (Sanyo Chemical), iron sesquioxide, and hydroxypropylmethylcellulose 2910 (TC-5, grade RW, Shin-Etsu Chemical) were dissolved or dispersed, thereby obtaining film tablets containing 10 mg of Compound A, 89.6 mg of D-mannitol, 16 mg of crystalline cellulose, 30 mg of fumaric acid, 4.8 mg of hydroxypropylcellulose, 8 mg of croscarmellose sodium, 1.6 mg of magnesium stearate, 5.8 mg of hydroxypropylmethylcellulose 2910, 1.4 mg of macrogol 6000, 0.6 mg of titanium oxide, and 0.2 mg of iron sesquioxide per a tablet.

Comparative Example 2

D-mannitol (515.7 g), and crystalline cellulose (64.3 g, CEOLUS, grade PH101, Asahi Kasei) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (385.7 g, grade L, Nippon Soda) in which Compound A (0.714 g) was dispersed, and thereafter dried to obtain granules. The obtained granules were made to pass through a sieve with mesh size of 850 μm to obtain main drug granules.

To main drug granules (400 g), croscarmellose sodium (22.4 g, Ac-Di-Sol) and magnesium stearate (6.2 g, Taihei Chemical Industrial) were added and mixed to obtain granules for tableting. The obtained granules were tabletted with a tableting machine using a round-shaped punch and die with a diameter of 6.0 mm to obtain 90 mg plain tablets. The obtained plain tablets were placed in a film coating machine (HICOATER, Freund Corporation), and sprayed with a liquid in which titanium oxide, macrogol 6000 (Sanyo Chemical), iron sesquioxide, and hydroxypropylmethylcellulose 2910 (TC-5, grade RW, Shin-Etsu Chemical) were dissolved or dispersed, thereby obtaining film tablets containing 0.1 mg of Compound A, 72.2 mg of D-mannitol, 9 mg of crystalline cellulose, 2.7 mg of hydroxypropylcellulose, 5.1 mg of croscarmellose sodium, 0.9 mg of magnesium stearate, 2.2 mg of hydroxypropylmethylcellulose 2910, 0.5 mg of macrogol 6000, 0.25 mg of titanium oxide, and 0.05 mg of iron sesquioxide per a tablet.

Comparative Example 3

D-mannitol (505 g), crystalline cellulose (64.3 g, CEOLUS, grade PH101, Asahi Kasei), and fumaric acid (10.7 g) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (385.7 g, grade L, Nippon Soda) in which Compound A (0.714 g) was dispersed, and thereafter dried to obtain granules. The obtained granules were made to pass through a sieve with mesh size of 850 μm to obtain main drug granules.

To main drug granules (150 g), croscarmellose sodium (8.4 g, Ac-Di-Sol) and magnesium stearate (1.6 g, Taihei Chemical Industrial) were added and mixed to obtain granules for tableting. The obtained granules were tabletted with a tableting machine using a round-shaped punch and die with a diameter of 6.0 mm to obtain 90 mg plain tablets. The obtained plain tablets were placed in a film coating machine (HICOATER, Freund Corporation), and sprayed with a liquid in which titanium oxide, macrogol 6000 (Sanyo Chemical), iron sesquioxide, and hydroxypropylmethylcellulose 2910 (TC-5, grade RW, Shin-Etsu Chemical) were dissolved or dispersed, thereby obtaining film tablets containing 0.1 mg of Compound A, 72.2 mg of D-mannitol, 9 mg of crystalline cellulose, 1.5 mg of fumaric acid, 2.7 mg of hydroxypropylcellulose, 5.1 mg of croscarmellose sodium, 0.9 mg of magnesium stearate, 2.2 mg of hydroxypropylmethylcellulose 2910, 0.5 mg of macrogol 6000, 0.25 mg of titanium oxide, and 0.05 mg of iron sesquioxide per a tablet.

Example 1

D-mannitol (514.3 g), and crystalline cellulose (64.3 g, CEOLUS, grade PH101, Asahi Kasei) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (371.4 g, grade L, Nippon Soda) in which Compound A (2.857 g) was dispersed, and thereafter dried to obtain granules. The obtained granules were made to pass through a sieve with mesh size of 850 μm to obtain main drug granules.

D-mannitol (501.9 g), crystalline cellulose (64.3 g, CEOLUS, grade PH101, Asahi Kasei) and fumaric acid (14.3 g) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (390.5 g, grade L, Nippon Soda), and thereafter dried to obtain granules. The obtained granules were made to pass through a sieve with mesh size of 850 μm to obtain fumaric acid granules.

To main drug granules (84 g), fumaric acid granules (252 g), croscarmellose sodium (20.4 g, Ac-Di-Sol) and magnesium stearate (3.6 g, Taihei Chemical Industrial) were added and mixed to obtain granules for tableting. The obtained granules were tabletted with a tableting machine using a round-shaped punch and die with a diameter of 6.0 mm to obtain 90 mg plain tablets. The obtained plain tablets were placed in a film coating machine (HICOATER, Freund Corporation), and sprayed with a liquid in which titanium oxide, macrogol 6000 (Sanyo Chemical), iron sesquioxide, and hydroxypropylmethylcellulose 2910 (TC-5, grade RW, Shin-Etsu Chemical) were dissolved or dispersed, thereby obtaining film tablets containing 0.1 mg of Compound A, 70.7 mg of D-mannitol, 9 mg of crystalline cellulose, 1.5 mg of fumaric acid, 2.7 mg of hydroxypropylcellulose, 5.1 mg of croscarmellose sodium, 0.9 mg of magnesium stearate, 2.2 mg of hydroxypropylmethylcellulose 2910, 0.5 mg of macrogol 6000, 0.25 mg of titanium oxide, and 0.05 mg of iron sesquioxide per a tablet.

Example 2

D-mannitol (515.7 g), and crystalline cellulose (64.3 g, CEOLUS, grade PH101, Asahi Kasei) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (385.7 g, grade L, Nippon Soda) in which Compound A (0.714 g) was dispersed, and thereafter dried to obtain granules. The obtained granules were made to pass through a sieve with mesh size of 850 μm to obtain main drug granules.

To main drug granules (250 g), fumaric acid (4.5 g), croscarmellose sodium (15.2 g, Ac-Di-Sol) and magnesium stearate (2.7 g, Taihei Chemical Industrial) were added and mixed to obtain granules for tableting. The obtained granules were tabletted with a tableting machine using a round-shaped punch and die with a diameter of 6.0 mm to obtain 91.5 mg plain tablets. The obtained plain tablets were placed in a film coating machine (HICOATER, Freund Corporation), and sprayed with a liquid in which titanium oxide, macrogol 6000 (Sanyo Chemical), iron sesquioxide, and hydroxypropylmethylcellulose 2910 (TC-5, grade RW, Shin-Etsu Chemical) were dissolved or dispersed, thereby obtaining film tablets containing 0.1 mg of Compound A, 72.2 mg of D-mannitol, 9 mg of crystalline cellulose, 1.5 mg of fumaric acid, 2.7 mg of hydroxypropylcellulose, 5.1 mg of croscarmellose sodium, 0.9 mg of magnesium stearate, 2.2 mg of hydroxypropylmethylcellulose 2910, 0.5 mg of macrogol 6000, 0.25 mg of titanium oxide, and 0.05 mg of iron sesquioxide per a tablet.

Example 3

D-mannitol (511.4 g), and crystalline cellulose (64.3 g, CEOLUS, grade PH101, Asahi Kasei) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (371.4 g, grade L, Nippon Soda) in which Compound A (5.714 g) was dispersed, and thereafter dried to obtain granules. The obtained granules were made to pass through a sieve with mesh size of 850 μm to obtain main drug granules.

D-mannitol (501.9 g), crystalline cellulose (64.3 g, CEOLUS, grade PH101, Asahi Kasei) and fumaric acid (14.3 g) were uniformly mixed, and the mixture was made to pass through a sieve with mesh size of 850 μm to uniformly mix again.

The resulting mixed powder was placed in a fluid bed granulator/dryer (LAB-1, Powrex), and granulated under fluidization while spraying an aqueous solution of 5% (wt./v) hydroxypropylcellulose (390.5 g, grade L, Nippon Soda), and thereafter dried to obtain granules. The obtained granules were made to pass through a sieve with mesh size of 850 μm to obtain fumaric acid granules.

To main drug granules (84 g), fumaric acid granules (252 g), croscarmellose sodium (20.4 g, Ac-Di-Sol) and magnesium stearate (3.6 g, Taihei Chemical Industrial) were added and mixed to obtain granules for tableting. The obtained granules were tabletted with a tableting machine using a round-shaped punch and die with a diameter of 6.0 mm to obtain 90 mg plain tablets. The obtained plain tablets were placed in a film coating machine (HICOATER, Freund Corporation), and sprayed with a liquid in which titanium oxide, macrogol 6000 (Sanyo Chemical), iron sesquioxide, and hydroxypropylmethylcellulose 2910 (TC-5, grade RW, Shin-Etsu Chemical) were dissolved or dispersed, thereby obtaining film tablets containing 0.2 mg of Compound A, 70.6 mg of D-mannitol, 9 mg of crystalline cellulose, 1.5 mg of fumaric acid, 2.7 mg of hydroxypropylcellulose, 5.1 mg of croscarmellose sodium, 0.9 mg of magnesium stearate, 2.2 mg of hydroxypropylmethylcellulose 2910, 0.5 mg of macrogol 6000, 0.25 mg of titanium oxide, and 0.05 mg of iron sesquioxide per a tablet.

Example 4

D-mannitol (508.6 g), and crystalline cellulose (64.3 g, CEOLUS, grade PH101, Asahi Kasei) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (371.4 g, grade L, Nippon Soda) in which Compound A (8.571 g) was dispersed, and thereafter dried to obtain granules. The obtained granules were made to pass through a sieve with mesh size of 850 μm to obtain main drug granules.

D-mannitol (501.9 g), crystalline cellulose (64.3 g, CEOLUS, grade PH101, Asahi Kasei) and fumaric acid (14.3 g) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (390.5 g, grade L, Nippon Soda), and thereafter dried to obtain granules. The obtained granules were made to pass through a sieve with mesh size of 850 μm to obtain fumaric acid granules.

To main drug granules (84 g), fumaric acid granules (252 g), croscarmellose sodium (20.4 g, Ac-Di-Sol) and magnesium stearate (3.6 g, Taihei Chemical Industrial) were added and mixed to obtain granules for tabletting. The obtained granules were tabletted with a tabletting machine using a round-shaped punch and die with a diameter of 6.0 mm to obtain 90 mg plain tablets. The obtained plain tablets were placed in a film coating machine (HICOATER, Freund Corporation), and sprayed with a liquid in which titanium oxide, macrogol 6000 (Sanyo Chemical), iron sesquioxide, and hydroxypropylmethylcellulose 2910 (TC-5, grade RW, Shin-Etsu Chemical) were dissolved or dispersed, thereby obtaining film tablets containing 0.3 mg of Compound A, 70.5 mg of D-mannitol, 9 mg of crystalline cellulose, 1.5 mg of fumaric acid, 2.7 mg of hydroxypropylcellulose, 5.1 mg of croscarmellose sodium, 0.9 mg of magnesium stearate, 2.2 mg of hydroxypropylmethylcellulose 2910, 0.5 mg of macrogol 6000, 0.25 mg of titanium oxide, and 0.05 mg of iron sesquioxide per a tablet.

Example 5

D-mannitol (502.9 g), and crystalline cellulose (64.3 g, CEOLUS, grade PH101, Asahi Kasei) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (371.4 g, grade L, Nippon Soda) in which Compound A (14.286 g) was dispersed, and thereafter dried to obtain granules. The obtained granules were made to pass through a sieve with mesh size of 850 μm to obtain main drug granules.

D-mannitol (501.9 g), crystalline cellulose (64.3 g, CEOLUS, grade PH101, Asahi Kasei) and fumaric acid (14.3 g) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (390.5 g, grade L, Nippon Soda), and thereafter dried to obtain granules. The obtained granules were made to pass through a sieve with mesh size of 850 μm to obtain fumaric acid granules.

To main drug granules (84 g), fumaric acid granules (252 g), croscarmellose sodium (20.4 g, Ac-Di-Sol) and magnesium stearate (3.6 g, Taihei Chemical Industrial) were added and mixed to obtain granules for tabletting. The obtained granules were tabletted with a tabletting machine using a round-shaped punch and die with a diameter of 6.0 mm to obtain 90 mg plain tablets. The obtained plain tablets were placed in a film coating machine (HICOATER, Freund Corporation), and sprayed with a liquid in which titanium oxide, macrogol 6000 (Sanyo Chemical), iron sesquioxide, and hydroxypropylmethylcellulose 2910 (TC-5, grade RW, Shin-Etsu Chemical) were dissolved or dispersed, thereby obtaining film tablets containing 0.5 mg of Compound A, 70.3 mg of D-mannitol, 9 mg of crystalline cellulose, 1.5 mg of fumaric acid, 2.7 mg of hydroxypropylcellulose, 5.1 mg of croscarmellose sodium, 0.9 mg of magnesium stearate, 2.2 mg of hydroxypropylmethylcellulose 2910, 0.5 mg of macrogol 6000, 0.25 mg of titanium oxide, and 0.05 mg of iron sesquioxide per a tablet.

Example 6

Compound A (45.0 g), D-mannitol (463.7 g), and crystalline cellulose (72.0 g, CEOLUS, grade PH101, Asahi Kasei) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (386.8 g, grade L, Nippon Soda), and thereafter dried to obtain granules. The obtained granules were made to pass through a sieve with mesh size of 850 μm to obtain main drug granules.

On the other hand, fumaric acid (352.9 g) and crystalline cellulose (35.3 g, CEOLUS, grade PH101, Asahi Kasei) were uniformly mixed. The resulting mixed powder was placed in a fluid bed granulator/dryer (LAB-1, Powrex), and granulated under fluidization while spraying an aqueous solution of 5% (wt./v) hydroxypropylcellulose (235.3 g, grade L, Nippon Soda), and thereafter dried to obtain granules. The obtained granules were made to pass through a sieve with mesh size of 850 μm to obtain fumaric acid granules.

To main drug granules (250.1 g), fumaric acid granules (31.9 g), croscarmellose sodium (15.0 g, Ac-Di-Sol) and magnesium stearate (3.0 g, Taihei Chemical Industrial) were added and mixed to obtain granules for tabletting. The obtained granules were tabletted with a tabletting machine using a round-shaped punch and die with a diameter of 7.5 mm to obtain 160 mg plain tablets. The obtained plain tablets were placed in a film coating machine (HICOATER, Freund Corporation), and sprayed with a liquid in which titanium oxide, macrogol 6000 (Sanyo Chemical), iron sesquioxide, and hydroxypropylmethylcellulose 2910 (TC-5, grade RW, Shin-Etsu Chemical) were dissolved or dispersed, thereby obtaining film tablets containing 10 mg of Compound A, 103.1 mg of D-mannitol, 17.5 mg of crystalline cellulose, 15 mg of fumaric acid, 4.8 mg of hydroxypropylcellulose, 8 mg of croscarmellose sodium, 1.6 mg of magnesium stearate, 5.8 mg of hydroxypropylmethylcellulose 2910, 1.4 mg of macrogol 6000, 0.6 mg of titanium oxide, and 0.2 mg of iron sesquioxide per a tablet.

Example 7

Compound A (45.0 g), D-mannitol (463.7 g), and crystalline cellulose (72.0 g, CEOLUS, grade PH101, Asahi Kasei) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (386.8 g, grade L, Nippon Soda), and thereafter dried to obtain granules. The obtained granules were made to pass through a sieve with mesh size of 850 μm to obtain main drug granules.

On the other hand, fumaric acid (352.9 g) and corn starch (35.3 g, Nihon Cornstarch) were uniformly mixed. The resulting mixed powder was placed in a fluid bed granulator/dryer (LAB-1, Powrex), and granulated under fluidization while spraying an aqueous solution of 5% (wt./v) hydroxypropylcellulose (235.3 g, grade L, Nippon Soda), and thereafter dried to obtain granules. The obtained granules were made to pass through a sieve with mesh size of 850 μm to obtain fumaric acid granules.

To main drug granules (250.1 g), fumaric acid granules (31.9 g), croscarmellose sodium (15.0 g, Ac-Di-Sol) and magnesium stearate (3.0 g, Taihei Chemical Industrial) were added and mixed to obtain granules for tableting. The obtained granules were tabletted with a tableting machine using a round-shaped punch and die with a diameter of 7.5 mm to obtain 160 mg plain tablets. The obtained plain tablets were placed in a film coating machine (HICOATER, Freund Corporation), and sprayed with a liquid in which titanium oxide, macrogol 6000 (Sanyo Chemical), iron sesquioxide, and hydroxypropylmethylcellulose 2910 (TC-5, grade RW, Shin-Etsu Chemical) were dissolved or dispersed, thereby obtaining film tablets containing 10 mg of Compound A, 103.1 mg of D-mannitol, 16 mg of crystalline cellulose, 1.5 mg of corn starch, 15 mg of fumaric acid, 4.8 mg of hydroxypropylcellulose, 8 mg of croscarmellose sodium, 1.6 mg of magnesium stearate, 5.8 mg of hydroxypropylmethylcellulose 2910, 1.4 mg of macrogol 6000, 0.6 mg of titanium oxide, and 0.2 mg of iron sesquioxide per a tablet.

Example 8

Compound A (45.0 g), D-mannitol (463.7 g), and crystalline cellulose (72.0 g, CEOLUS, grade PH101, Asahi Kasei) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (386.8 g, grade L, Nippon Soda), and thereafter dried to obtain granules. The obtained granules were made to pass through a sieve with mesh size of 850 μm to obtain main drug granules.

On the other hand, fumaric acid (352.9 g) and heavy, low substituted hydroxypropylcellulose (35.3 g, LH-B1, Shin-Etsu Chemical) were uniformly mixed. The resulting mixed powder was placed in a fluid bed granulator/dryer (LAB-1, Powrex), and granulated under fluidization while spraying an aqueous solution of 10% (wt./v) polyvinylpyrrolidone (117.6 g, Kollidon 25, BASF Takeda), and thereafter dried to obtain granules. The obtained granules were made to pass through a sieve with mesh size of 850 μm to obtain fumaric acid granules.

To main drug granules (250.1 g), fumaric acid granules (31.9 g), croscarmellose sodium (15.0 g, Ac-Di-Sol) and magnesium stearate (3.0 g, Taihei Chemical Industrial) were added and mixed to obtain granules for tableting. The obtained granules were tabletted with a tableting machine using a round-shaped punch and die with a diameter of 7.5 mm to obtain 160 mg plain tablets. The obtained plain tablets were placed in a film coating machine (HICOATER, Freund Corporation), and sprayed with a liquid in which titanium oxide, macrogol 6000 (Sanyo Chemical), iron sesquioxide, and hydroxypropylmethylcellulose 2910 (TC-5, grade RW, Shin-Etsu Chemical) were dissolved or dispersed, thereby obtaining film tablets containing 10 mg of Compound A, 103.1 mg of D-mannitol, 16 mg of crystalline cellulose, 1.5 mg of heavy, low substituted hydroxypropylcellulose, 15 mg of fumaric acid, 4.3 mg of hydroxypropylcellulose, 0.5 mg of polyvinylpyrrolidone, 8 mg of croscarmellose sodium, 1.6 mg of magnesium stearate, 5.8 mg of hydroxypropylmethylcellulose 2910, 1.4 mg of macrogol 6000, 0.6 mg of titanium oxide, and 0.2 mg of iron sesquioxide per a tablet.

Example 9

Compound A (45.0 g), D-mannitol (463.7 g), and crystalline cellulose (72.0 g, CEOLUS, grade PH101, Asahi Kasei) were uniformly mixed, and the mixture was made to pass through a sieve with mesh size of 850 μm to uniformly mix again. The resulting mixed powder was placed in a fluid bed granulator/dryer (LAB-1, Powrex), and granulated under fluidization while spraying an aqueous solution of 5% (wt./v) hydroxypropylcellulose (386.8 g, grade L, Nippon Soda), and thereafter dried to obtain granules. The obtained granules were made to pass through a sieve with mesh size of 850 μM to obtain main drug granules.

On the other hand, fumaric acid (352.9 g) and corn starch (35.3 g, Nihon Cornstarch) were uniformly mixed. The resulting mixed powder was placed in a fluid bed granulator/dryer (LAB-1, Powrex), and granulated under fluidization while spraying an aqueous solution of 5% (wt./v) hydroxypropylcellulose (235.3 g, grade SLT, Nippon Soda), and thereafter dried to obtain granules. The obtained granules were made to pass through a sieve with mesh size of 850 μm to obtain fumaric acid granules.

To main drug granules (250.1 g), fumaric acid granules (31.9 g), croscarmellose sodium (15.0 g, Ac-Di-Sol) and magnesium stearate (3.0 g, Taihei Chemical Industrial) were added and mixed to obtain granules for tableting. The obtained granules were tabletted with a tableting machine using a round-shaped punch and die with a diameter of 7.5 mm to obtain 160 mg plain tablets. The obtained plain tablets were placed in a film coating machine (HICOATER, Freund Corporation), and sprayed with a liquid in which titanium oxide, macrogol 6000 (Sanyo Chemical), iron sesquioxide, and hydroxypropylmethylcellulose 2910 (TC-5, grade RW, Shin-Etsu Chemical) were dissolved or dispersed, thereby obtaining film tablets containing 10 mg of Compound A, 103.1 mg of D-mannitol, 16 mg of crystalline cellulose, 1.5 mg of heavy, low substituted hydroxypropylcellulose, 15 mg of fumaric acid, 4.3 mg of hydroxypropylcellulose, 0.5 mg of polyvinylpyrrolidone, 8 mg of croscarmellose sodium, 1.6 mg of magnesium stearate, 5.8 mg of hydroxypropylmethylcellulose 2910, 1.4 mg of macrogol 6000, 0.6 mg of titanium oxide, and 0.2 mg of iron sesquioxide per a tablet.

Example 10

D-mannitol (4320 g) and crystalline cellulose (540 g, CEOLUS, grade PH101, Asahi Kasei) were placed in a fluid bed granulator/dryer (LAB-1, Powrex), and granulated under fluidization while spraying a liquid prepared by dispersing Compound A (24 g) in a solution of hydroxypropylcellulose (156 g, grade L, Nippon Soda) in purified water (2592 g), and thereafter dried to obtain granules. The obtained granules were subjected to size selection using a power mill (mesh 1.5 mm) to obtain main drug granules.

On the other hand, fumaric acid (120 g), D-mannitol (4216 g) and crystalline cellulose (540 g, CEOLUS, grade PH101, Asahi Kasei) were uniformly mixed. The resulting mixed powder was placed in a fluid bed granulator/dryer, and granulated under fluidization while spraying a solution of hydroxypropylcellulose (164 g, grade L, Nippon Soda) in purified water (2736 g), and thereafter dried to obtain granules. The obtained granules were subjected to size selection using a power mill (mesh 1.5 mm) to obtain fumaric acid granules.

To main drug granules (1365 g), fumaric acid granules (4095 g), croscarmellose sodium (331.5 g, Ac-Di-Sol) and magnesium stearate (58.5 g, Taihei Chemical Industrial) were added and mixed to obtain granules for tableting. The obtained granules were tabletted with a tableting machine using a round-shaped punch and die with a diameter of 6.0 mm to obtain 90 mg plain tablets. The obtained plain tablets were placed in a film coating machine, and sprayed with a liquid in which titanium oxide, macrogol 6000 (Sanyo Chemical), iron sesquioxide, yellow iron sesquioxide and hydroxypropylmethylcellulose 2910 (TC-5, grade RW, Shin-Etsu Chemical) were dissolved or dispersed, thereby obtaining film tablets containing 0.1 mg of Compound A, 70.7 mg of D-mannitol, 9 mg of crystalline cellulose, 1.5 mg of fumaric acid, 2.7 mg of hydroxypropylcellulose, 5.1 mg of croscarmellose sodium, 0.9 mg of magnesium stearate, 2.196 mg of hydroxypropylmethylcellulose 2910, 0.48 mg of macrogol 6000, 0.3 mg of titanium oxide, 0.012 mg of iron sesquioxide, and 0.012 mg of yellow iron sesquioxide per a tablet.

Example 11

D-mannitol (4295 g) and crystalline cellulose (540 g, CEOLUS, grade PH101, Asahi Kasei) were placed in a fluid bed granulator/dryer, and granulated under fluidization while spraying a liquid prepared by dispersing Compound A (48 g) in a solution of hydroxypropylcellulose (156 g, grade L, Nippon Soda) in purified water (2592 g), and thereafter dried to obtain granules. The obtained granules were subjected to size selection using a power mill (mesh 1.5 mm) to obtain main drug granules.

On the other hand, fumaric acid (120 g), D-mannitol (4216 g) and crystalline cellulose (540 g, CEOLUS, grade PH101, Asahi Kasei) were uniformly mixed. The resulting mixed powder was placed in a fluid bed granulator/dryer, and granulated under fluidization while spraying a solution of hydroxypropylcellulose (164 g, grade L, Nippon Soda) in purified water (2736 g), and thereafter dried to obtain granules. The obtained granules were subjected to size selection using a power mill (mesh 1.5 mm) to obtain fumaric acid granules.

To main drug granules (1365 g), fumaric acid granules (4095 g), croscarmellose sodium (331.5 g, Ac-Di-Sol) and magnesium stearate (58.5 g, Taihei Chemical Industrial) were added and mixed to obtain granules for tableting. The obtained granules were tabletted with a tableting machine using a round-shaped punch and die with a diameter of 6.0 mm to obtain 90 mg plain tablets. The obtained plain tablets were placed in a film coating machine, and sprayed with a liquid in which titanium oxide, macrogol 6000 (Sanyo Chemical), iron sesquioxide, yellow iron sesquioxide and hydroxypropylmethylcellulose 2910 (TC-5, grade RW, Shin-Etsu Chemical) were dissolved or dispersed, thereby obtaining film tablets containing 0.2 mg of Compound A, 70.6 mg of D-mannitol, 9 mg of crystalline cellulose, 1.5 mg of fumaric acid, 2.7 mg of hydroxypropylcellulose, 5.1 mg of croscarmellose sodium, 0.9 mg of magnesium stearate, 2.196 mg of hydroxypropylmethylcellulose 2910, 0.48 mg of macrogol 6000, 0.3 mg of titanium oxide, 0.012 mg of iron sesquioxide, and 0.012 mg of yellow iron sesquioxide per a tablet.

Example 12

D-mannitol (4271 g) and crystalline cellulose (540 g, CEOLUS, grade PH101, Asahi Kasei) were placed in a fluid bed granulator/dryer, and granulated under fluidization while spraying a liquid prepared by dispersing Compound A (72 g) in a solution of hydroxypropylcellulose (156 g, grade L, Nippon Soda) in purified water (2592 g), and thereafter dried to obtain granules. The obtained granules were subjected to size selection using a power mill (mesh 1.5 mm) to obtain main drug granules.

On the other hand, fumaric acid (120 g), D-mannitol (4216 g) and crystalline cellulose (540 g, CEOLUS, grade PH101, Asahi Kasei) were uniformly mixed. The resulting mixed powder was placed in a fluid bed granulator/dryer, and granulated under fluidization while spraying a solution of hydroxypropylcellulose (164 g, grade L, Nippon Soda) in purified water (2736 g), and thereafter dried to obtain granules. The obtained granules were subjected to size selection using a power mill (mesh 1.5 mm) to obtain fumaric acid granules.

To main drug granules (1365 g), fumaric acid granules (4095 g), croscarmellose sodium (331.5 g, Ac-Di-Sol) and magnesium stearate (58.5 g, Taihei Chemical Industrial) were added and mixed to obtain granules for tableting. The obtained granules were tabletted with a tableting machine using a round-shaped punch and die with a diameter of 6.0 mm to obtain 90 mg plain tablets. The obtained plain tablets were placed in a film coating machine, and sprayed with a liquid in which titanium oxide, macrogol 6000 (Sanyo Chemical), iron sesquioxide, yellow iron sesquioxide and hydroxypropylmethylcellulose 2910 (TC-5, grade RW, Shin-Etsu Chemical) were dissolved or dispersed, thereby obtaining film tablets containing 0.3 mg of Compound A, 70.5 mg of D-mannitol, 9 mg of crystalline cellulose, 1.5 mg of fumaric acid, 2.7 mg of hydroxypropylcellulose, 5.1 mg of croscarmellose sodium, 0.9 mg of magnesium stearate, 2.196 mg of hydroxypropylmethylcellulose 2910, 0.48 mg of macrogol 6000, 0.3 mg of titanium oxide, 0.012 mg of iron sesquioxide, and 0.012 mg of yellow iron sesquioxide per a tablet.

Example 13

Compound A (21 g), D-mannitol (4935 g) and crystalline cellulose (630 g, CEOLUS, grade PH101, Asahi Kasei) were placed in a fluid bed granulator/dryer, and granulated under fluidization while spraying a solution of hydroxypropylcellulose (189 g, grade L, Nippon Soda) in purified water (2961 g), and thereafter dried to obtain granules. The obtained granules were subjected to size selection using a power mill (mesh 1.5 mm) to obtain main drug granules.

To main drug granules (5198 g), fumaric acid (94.5 g), croscarmellose sodium (296.1 g, Ac-Di-Sol) and magnesium stearate (81.9 g, Taihei Chemical Industrial) were added and mixed to obtain granules for tableting. The obtained granules were tabletted with a tableting machine using a round-shaped punch and die with a diameter of 6.0 mm to obtain 90 mg plain tablets. The obtained plain tablets were placed in a film coating machine, and sprayed with a liquid in which titanium oxide, macrogol 6000 (Sanyo Chemical), iron sesquioxide, yellow iron sesquioxide and hydroxypropylmethylcellulose 2910 (TC-5, grade RW, Shin-Etsu Chemical) were dissolved or dispersed, thereby obtaining film tablets containing 0.3 mg of Compound A, 70.5 mg of D-mannitol, 9 mg of crystalline cellulose, 1.5 mg of fumaric acid, 2.7 mg of hydroxypropylcellulose, 4.7 mg of croscarmellose sodium, 1.3 mg of magnesium stearate, 2.196 mg of hydroxypropylmethylcellulose 2910, 0.48 mg of macrogol 6000, 0.3 mg of titanium oxide, 0.012 mg of iron sesquioxide, and 0.012 mg of yellow iron sesquioxide per a tablet.

Example 14

Compound A (21 g), D-mannitol (4935 g) and crystalline cellulose (630 g, CEOLUS, grade PH101, Asahi Kasei) were placed in a fluid bed granulator/dryer, and granulated under fluidization while spraying a solution of hydroxypropylcellulose (189 g, grade L, Nippon Soda) in purified water (2961 g), and thereafter dried to obtain granules. The obtained granules were subjected to size selection using a power mill (mesh 1.5 mm) to obtain main drug granules.

To main drug granules (5198 g), carboxymethylcellulose (296.1 g, NS-300), and magnesium stearate (81.9 g, Taihei Chemical Industrial) were added and mixed to obtain granules for tableting. The obtained granules were tabletted with a tableting machine using a round-shaped punch and die with a diameter of 6.0 mm to obtain 88.5 mg plain tablets. The obtained plain tablets were placed in a film coating machine, and sprayed with a liquid in which titanium oxide, macrogol 6000 (Sanyo Chemical), iron sesquioxide, yellow iron sesquioxide and hydroxypropylmethylcellulose 2910 (TC-5, grade RW, Shin-Etsu Chemical) were dissolved or dispersed, thereby obtaining film tablets containing 0.3 mg of Compound A, 70.5 mg of D-mannitol, 9 mg of crystalline cellulose, 2.7 mg of hydroxypropylcellulose, 4.7 mg of carboxymethylcellulose, 1.3 mg of magnesium stearate, 2.196 mg of hydroxypropylmethylcellulose 2910, 0.48 mg of macrogol 6000, 0.3 mg of titanium oxide, 0.012 mg of iron sesquioxide, and 0.012 mg of yellow iron sesquioxide per a tablet.

In the examples, Compound A was used after pulverized with a SK JET-O-MILL (JOM-0101, Seishin Enterprise). The particle size of the pulverized Compound A measured with a laser diffraction analyzer for dry measurement (Mastersizer 2000, Malvern) was D10:1.4 µm, D50: 5.6 µm, D90: 12.0 µm.

The particle size of the fumaric acid used in the examples was D10: 22 µm, D50: 80 µm, D90: 150 µm.

Experiment 1 (Specific Volume, Particle Size Distribution)

For measurement of specific volume, 50 g of each of main drug granules and fumaric acid granules was weighed out, and the volume thereof was measured with a graduated cylinder.

For measurement of particle size distribution, 50 g of each of main drug granules and fumaric acid granules was weighed out and classified using a standard sieve, and the classified particles were weighed up.

TABLE 1

Specific Volume and Particle Size Distribution

| Sample Name | Main drug granule | Fumaric acid granule |
|---|---|---|
| Apparent specific volume (ml/g) | 2.8 | 3.0 |
| Tapped specific volume (ml/g) | 2.3 | 2.4 |
| 30 mesh on (%) | 0.0 | 0.0 |
| 42 mesh on (%) | 0.6 | 1.8 |
| 60 mesh on (%) | 5.1 | 13.8 |
| 100 mesh on (%) | 31.9 | 44.1 |
| 100 mesh pass (%) | 62.4 | 40.2 |

Table 1 shows the specific volume and the particle size distribution of the main drug granules (size selected) and fumaric acid granules (size selected) described in Example 1.

TABLE 2

Specific Volume

| | | Example 10 | Example 11 | Example 12 |
|---|---|---|---|---|
| Main drug granule | Apparent specific volume (ml/g) | 2.4 | 2.5 | 2.4 |
| | Tapped specific volume (ml/g) | 2.0 | 2.0 | 2.0 |
| Fumaric acid granule | Apparent specific volume (ml/g) | 2.4 | 2.5 | 2.5 |
| | Tapped specific volume (ml/g) | 2.0 | 2.0 | 2.0 |

TABLE 3

Particle Size Distribution

| | Main drug granule | Fumaric acid granule |
|---|---|---|
| Example 10 | | |
| 16 mesh on (%) | 0.0 | 0.0 |
| 30 mesh on (%) | 7.4 | 8.4 |
| 42 mesh on (%) | 13.8 | 14.0 |
| 60 mesh on (%) | 21.2 | 20.4 |
| 100 mesh on (%) | 30.6 | 29.4 |
| 100 mesh pass (%) | 27.0 | 27.4 |
| Example 11 | | |
| 16 mesh on (%) | 0.0 | 0.0 |
| 30 mesh on (%) | 12.0 | 6.6 |
| 42 mesh on (%) | 14.6 | 14.6 |
| 60 mesh on (%) | 18.6 | 23.6 |
| 100 mesh on (%) | 25.4 | 28.4 |
| 100 mesh pass (%) | 27.8 | 26.8 |
| Example 12 | | |
| 16 mesh on (%) | 0.0 | 0.0 |
| 30 mesh on (%) | 9.0 | 10.4 |
| 42 mesh on (%) | 12.8 | 13.8 |
| 60 mesh on (%) | 17.4 | 21.2 |
| 100 mesh on (%) | 26.0 | 27.6 |
| 100 mesh pass (%) | 33.6 | 27.2 |

TABLE 4

| | Amount Based on Indicated Content (%) |
|---|---|
| | Example 10 |
| 30 mesh on (%) | 109.8 |
| 42 mesh on (%) | 108.1 |

TABLE 4-continued

| | Amount Based on Indicated Content (%) |
|---|---|
| 60 mesh on (%) | 105.6 |
| 100 mesh on (%) | 101.3 |
| 100 mesh pass (%) | 88.8 |
| Example 11 | |
| 30 mesh on (%) | 110.0 |
| 42 mesh on (%) | 107.6 |
| 60 mesh on (%) | 105.3 |
| 100 mesh on (%) | 101.4 |
| 100 mesh pass (%) | 93.4 |
| Example 12 | |
| 30 mesh on (%) | 107.9 |
| 42 mesh on (%) | 107.4 |
| 60 mesh on (%) | 105.0 |
| 100 mesh on (%) | 102.1 |
| 100 mesh pass (%) | 94.1 |

Tables 2 and 3 show the specific volume and the particle size distribution of the main drug granules and fumaric acid granules described in Examples 10, 11 and 12. Table 4 shows the content of each particle size of the main drug granules described in Examples 10, 11 and 12.

Experiment 2 (Dissolution Test)

The dissolution test was carried out in accordance with the paddle method described in the Japanese pharmacopoeia, 14th Edition, i.e., paddle speed: 50, 100, 250 rpm, test fluid temperature: 37° C., test fluid: the second fluid of the disintegration test described in Japanese Pharmacopoeia, 14th Edition. At 5, 30 and 60 minutes after the start of the test, 3 mL aliquot of the test fluid was collected through a fine filter (F-72, produced by Toyama Sangyo), and filtered using a syringe filter (Nihon Pall, Acrodisc LC25, PVDF, pore size: 0.45 μm). Two milliliter of the initial filtrate was discarded, and the concentration of Compound A in the remaining filtrate was measured by HPLC. The concentration was converted into the release ratio.

(HPLC Conditions)
1) Column: Trade name YMC-Pack Pro C18 (produced by YMC)
   Filler particle size: 5 μm.
   Column size: 3.01 mmϕ×50 mm.
2) Eluent: 20 mM $KH_2PO_4$/MeCN=8/2 (v/v).
3) Wavelength: UV 221 nm.
4) Flow rate: 0.7 mL/min.
5) Injection cycle: 8 min.
6) Injection volume: 50 μL.

TABLE 5

Release Ratio (%) of Comparative Example 1-1

| | Time (min) | | |
|---|---|---|---|
| Paddle speed | 5 | 30 | 60 |
| 50 rpm. | 39 | 82 | 83 |
| 100 rpm. | 45 | 79 | 86 |
| 250 rpm. | 55 | 77 | 83 |

TABLE 6

Release Ratio (%), Paddle Speed: 50 rpm.

| | Time (min) | | |
|---|---|---|---|
| Preparation | 5 | 30 | 60 |
| Comparative Example 1-1 | 39 | 82 | 83 |
| Comparative Example 1-2 | 43 | 99 | 101 |

The release ratio of Comparative Example 1-1, which did not contain fumaric acid, reached its plateau of about 80% at 30-60 minutes after the start of the dissolution test (Table 5). On the other hand, Comparative Example 1-2, which contained fumaric acid, showed an improved release ratio and had a good release profile (Table 6).

These results indicate that an accelerated release, an improved release ratio, and a good release profile can be obtained by adding an optimal amount of fumaric acid to tablets.

Experiment 3 (Shelf Stability: Amount of Related Substances)

Storage condition: 40° C./33% RH, opened, and Storage period: 1 month were employed in this experiment. The amount of the generated related substances was measured as follows. That is, 5 film tablets were added to 250 mL of extraction solution, and the solution was shaken to break the tablets. The solution was then sonicated and filtered through a syringe filter (Nihon Pall, Acrodisc LC25, PVDF, pore size: 0.45 μm). Two milliliter of the initial filtrate was discarded, and the concentration of the related substances in the remaining filtrate was measured by HPLC. The concentration was converted into the release ratio.

Eluent: 50 mM $KH_2PO_4$ (pH2)/MeCN=8/2 (v/v).

(HPLC Conditions)
1) Column: YMC-Pack Pro C18 (produced by YMC)
   Filler particle size: 5 μm.
   Column size: 3.0 mmϕ×250 mm.
2) Eluent A: 50 mM $KH_2PO_4$/MeCN=97.5/2.5 (v/v).
   Eluent B: 50 mM $KH_2PO_4$/MeCN=40/60 (v/v).
   Gradient: ratio of Eluent B
   0-20 min.:0%
   20-65 min.:0-70%
   65-75 min.: 70-100%
   75-90 min.:0%
3) Column temperature: 40° C.
4) Wavelength: UV 210 nm.
5) Flow rate: 0.5 mL/min.
6) Injection cycle: 90 min.
7) Injection volume: 50 μL.

TABLE 7

Amount of Related Substances

|  | Storage condition | RRT0.8 (%) | RRT0.88 (%) | RRT0.92 (%) | RRT1.1 (%) | Total related substances (%) |
|---|---|---|---|---|---|---|
| Comparative Example 2 | int. | 0.02 | 0.13 | 0.03 | 0.12 | 0.44 |
|  | 40° C./33% RH 1M | 0.02 | 0.16 | 0.04 | 0.17 | 0.50 |
| Comparative Example 3 | int. | 0.03 | 0.12 | 0.02 | 0.13 | 0.45 |
|  | 40° C./33% RH 1M | 0.06 | 0.21 | 0.16 | 0.22 | 0.77 |
| Example 1 | int. | 0.03 | 0.14 | 0.04 | 0.12 | 0.46 |
|  | 40° C./33% RH 1M | 0.03 | 0.20 | 0.04 | 0.15 | 0.53 |

As shown in Table 7, comparing Comparative Example 2 which did not contain fumaric acid with Comparative Example 3 which contained fumaric acid, the amount of related substances increased from 0.50% to 0.77%. Among the groups of related substances classified by relative retention time (RRT), RRT0.92 group notably increased from 0.04% to 0.16%.

This result indicates that the shelf stability becomes worse when fumaric acid is simply added.

However, Example 1, in which Compound A and fumaric acid were separately added, was stable similarly to Comparative Example 2 which did not contain fumaric acid.

This result clearly indicates that deterioration of shelf stability can be suppressed by separately adding fumaric acid.

TABLE 8

Release Ratio (%), Paddle Speed: 50 rpm.

|  | Time (min) | | |
|---|---|---|---|
| Preparation | 5 | 30 | 60 |
| Comparative Example 3 | 78 | 97 | 100 |
| Example 2 | 77 | 100 | 99 |
| Example 3 | 80 | 96 | 97 |
| Example 4 | 79 | 99 | 100 |
| Example 5 | 77 | 99 | 100 |

The foregoing paragraph confirms that deterioration of shelf stability can be suppressed by adding fumaric acid separately from Compound A. Next experiment was carried out to investigate whether the release profile is improved as intended or not.

As shown in Table 8, the tablets with various doses in which fumaric acid was separately added successfully achieved a good release profile equal to that of Comparative Example 3 in which fumaric acid was simply added.

Thus, improvement of the release profile and suppression of deterioration of shelf stability could be achieved at the same time by separately adding an optimal amount of fumaric acid.

Experiment 4 (Shelf Stability: Dissolution Test)

Storage condition: 40° C./33% RH or 40° C./75% RH, opened, and Storage period: 2 months were employed in this experiment. The dissolution test was carried out in the same manner as in Experiment 2 except that phosphate buffer pH6.0 was used as a test fluid.

TABLE 9

Release Ratio (%) of Example 1, Paddle Speed: 50 rpm.

|  | Time (min) | | |
|---|---|---|---|
| Storage condition | 5 | 30 | 60 |
| int. | 95 | 100 | 100 |
| 40° C./33% RH 2M | 98 | 101 | 100 |
| 40° C./75% RH 2M | 95 | 98 | 99 |

TABLE 10

Release Ratio (%) of Example 5, Paddle Speed: 50 rpm.

|  | Time (min) | | |
|---|---|---|---|
| Storage condition | 5 | 30 | 60 |
| int. | 97 | 100 | 102 |
| 40° C./33% RH 2M | 89 | 95 | 98 |
| 40° C./75% RH 2M | 97 | 98 | 102 |

Tables 9 and 10 show the shelf stability based on the release profile. Examples 1 and 5 kept a good release profile even after storage.

This application claims the priority of Japanese patent application No. 2007-134421, the entire contents of which are hereby incorporated by reference.

The invention claimed is:

1. A process for producing tablets containing fumaric acid and a morphinan compound, which is N-[(5R,6R,14S)-17-(cyclopropylmethyl)-4,5-epoxy-3,14-dihyroxymorphinan-6-yl]phthalimide or a pharmaceutically acceptable acid addition salt thereof, which process comprises
    granulating by wet granulation the morphinan compound or a pharmaceutically acceptable acid addition salt thereof together with (an) excipient(s) and separately granulating fumaric acid by wet granulation together with (an) excipient(s) prior to adding fumaric acid, in an amount of 0.01 to 500 parts by weight per 1 part by weight of the morphinan compound or a pharmaceutically acceptable acid addition salt thereof, thereto in the form of a fine powder, not less than 90% by weight of which has a particle size of not more than 355 μm.

2. The process according to claim 1, wherein the content of fumaric acid is 0.001 to 85% (w/w) based on the entire tablet.

3. The process according to claim 1, wherein the content of fumaric acid is 0.001 to 85% (w/w) based on a plain tablet.

4. The process according to claim 1, wherein a fine powder, not less than 90% by weight of which has a particle size of not more than 250 μm, is used as fumaric acid.

5. The process according to claim 1, wherein a powder of fumaric acid is added.

6. The process according to claim 1, wherein a solution or a partially dissolved suspension of fumaric acid is added.

7. A tablet obtained by the process according to claim 1.

8. A tablet produced by adding fumaric acid to granules containing a morphinan compound, which is N-[(5R,6R,14S)-17-(cyclopropylmethyl)-4,5-epoxy-3,14-dihyroxy-morphinan-6-yl]phthalimide or a pharmaceutically acceptable acid addition salt thereof, wherein the granules are made by wet granulation.

9. The tablet according to claim 8, produced by granulating by wet granulation the morphinan compound or a pharmaceutically acceptable acid addition salt thereof together with (an) excipient(s) prior to adding the fumaric acid thereto.

* * * * *